US009013478B2

(12) United States Patent
Chang et al.

(10) Patent No.: US 9,013,478 B2
(45) Date of Patent: Apr. 21, 2015

(54) METHOD AND APPARATUS FOR DISPLAYING STEREOSCOPIC INFORMATION RELATED TO ULTRASOUND SECTIONAL PLANE OF TARGET OBJECT (71) Applicants: Samsung Electronics Co., Ltd., Suwon-si (KR); Samsung Medison Co., Ltd., Gangwon-do (KR)

(72) Inventors: Eun-jung Chang, Ansan-si (KR); Jin-yong Lee, Seoul (KR)

(73) Assignees: Samsung Electronics Co., Ltd., Suwon-si (KR); Samsung Medison Co., Ltd., Gangwon-do (KR)

( * ) Notice: Subject to any disclaimer, the term of this patent is extended or adjusted under 35 U.S.C. 154(b) by 0 days.

(21) Appl. No.: 14/020,075

(22) Filed: Sep. 6, 2013

(65) Prior Publication Data
US 2014/0063006 A1 Mar. 6, 2014

(30) Foreign Application Priority Data

Sep. 6, 2012 (KR) .................... 10-2012-0098962
Jun. 21, 2013 (KR) .................... 10-2013-0071955

(51) Int. Cl.
*G06T 15/00* (2011.01)
*A61B 8/08* (2006.01)
*A61B 8/00* (2006.01)
*G01S 7/52* (2006.01)
*A61B 8/13* (2006.01)

(52) U.S. Cl.
CPC . *A61B 8/483* (2013.01); *A61B 8/13* (2013.01); *A61B 8/466* (2013.01); *A61B 8/469* (2013.01); *A61B 8/486* (2013.01); *G01S 7/52066* (2013.01); *G01S 7/52068* (2013.01); *G01S 7/52071* (2013.01); *G01S 7/52074* (2013.01)

(58) Field of Classification Search
None
See application file for complete search history.

(56) References Cited

U.S. PATENT DOCUMENTS

| 5,355,887 | A |   | 10/1994 | Iizuka et al. |
|-----------|---|---|---------|------|
| 5,515,856 | A |   | 5/1996  | Olstad et al. |
| 5,766,129 | A | * | 6/1998  | Mochizuki ............... 600/443 |
| 6,177,923 | B1 | * | 1/2001 | Arenson et al. .......... 345/589 |

(Continued)

FOREIGN PATENT DOCUMENTS

| JP | 4-17842 A | 1/1992 |
| JP | 11-327 A | 1/1999 |

(Continued)

OTHER PUBLICATIONS

International Search Report, dated for Dec. 11, 2013, issused by the International Searching Authority in counterpart International Application No. PCT/KR2013/007723.

(Continued)

*Primary Examiner* — James A Thompson
*Assistant Examiner* — Xilin Guo
(74) *Attorney, Agent, or Firm* — Sughrue Mion, PLLC (57) ABSTRACT A method of displaying stereoscopic information related to an ultrasound sectional plane of a target object includes: setting a line of interest on the target object; obtaining brightness information of the ultrasound sectional plane of the target object along the set line of interest; converting the obtained brightness information into height information; and displaying the stereoscopic information related to the ultrasound sectional plane of the target object based on the height information.

17 Claims, 9 Drawing Sheets

(56) References Cited

U.S. PATENT DOCUMENTS

| | | | |
|---|---|---|---|
| 2001/0048440 | A1 | 12/2001 | Wiesauer |
| 2005/0240104 | A1 | 10/2005 | Shim et al. |
| 2006/0155187 | A1* | 7/2006 | Zhao et al. .................. 600/419 |
| 2008/0009734 | A1 | 1/2008 | Houle et al. |
| 2010/0113930 | A1* | 5/2010 | Miyachi ...................... 600/443 |
| 2010/0185092 | A1* | 7/2010 | Yao et al. .................... 600/443 |
| 2010/0198073 | A1* | 8/2010 | Nishihara et al. ............ 600/443 |
| 2010/0312112 | A1* | 12/2010 | Kamiyama .................. 600/443 |
| 2011/0004101 | A1* | 1/2011 | Yang et al. ................... 600/443 |
| 2011/0273667 | A1* | 11/2011 | Knighton et al. ............ 351/206 |
| 2012/0045101 | A1 | 2/2012 | Everett et al. |
| 2012/0087564 | A1* | 4/2012 | Tsujita ........................ 382/131 |
| 2012/0113108 | A1* | 5/2012 | Dala-Krishna .............. 345/419 |

FOREIGN PATENT DOCUMENTS

| | | |
|---|---|---|
| JP | 2012-143332 A | 8/2012 |
| KR | 10-2002-0083685 A | 11/2002 |
| KR | 10-0686289 B1 | 2/2007 |

OTHER PUBLICATIONS

Written Opinion, dated for Dec. 11, 2013, issued by the International Searching Authority in counterpart International Application No. PCT/KR2013/007723.

Communication, dated for Jan. 16, 2014, issued by the European Patent Office in counterpart European Application No. 13183335.2.

* cited by examiner

FIG. 10

METHOD AND APPARATUS FOR DISPLAYING STEREOSCOPIC INFORMATION RELATED TO ULTRASOUND SECTIONAL PLANE OF TARGET OBJECT

CROSS-REFERENCE TO RELATED PATENT APPLICATION

This application claims priority from Korean Patent Applications No. 10-2012-0098962, filed on Sep. 6, 2012, and No. 10-2013-0071955, filed on Jun. 21, 2013, in the Korean Intellectual Property Office, the disclosures of which are incorporated herein by reference in their entireties.

BACKGROUND

1. Field

Apparatuses and methods consistent with exemplary embodiments relate to a method and apparatus for displaying stereoscopic information related to an ultrasound sectional plane of a target object, and more particularly, to a method and apparatus for converting information related to an ultrasound sectional plane into stereoscopic information by using ultrasound data and displaying the stereoscopic information.

2. Description of the Related Art

An ultrasonic diagnosis apparatus transfers an ultrasonic wave signal from a body surface toward a predetermined portion inside a body, i.e., a target object, to obtain an image of a cross-section of hematoceles of soft tissue by using information of the ultrasonic wave signal that is reflected by the tissue inside the body.

The ultrasonic diagnosis apparatus is compact, inexpensive, and displays images in real-time. In addition, the ultrasonic diagnosis apparatus does not cause exposure to radiation, for example, X-rays, and is thus stable and may be widely used with other imaging diagnosis apparatuses such as an X-ray diagnosis apparatus, a computerized tomography (CT) scanner, a magnetic resonance imaging apparatus, or a nuclear medical diagnosis apparatus.

An ultrasound image obtained by an ultrasonic diagnosis apparatus may be utilized to obtain various measurements such as a hardness, a size, a volume, a hematoceles moving velocity, etc. of tissue. To precisely measure a target object, it is required to clearly understand information regarding tissue such as boundary lines of tissue, movement of boundary lines, etc. Thus, to obtain precise information regarding the target object, for example, tissue, information regarding an ultrasound sectional plane of the target object may be utilized.

SUMMARY

The present invention provides a method and apparatus for displaying stereoscopic information related to an ultrasound sectional plane of a target object.

According to an aspect of an exemplary embodiment, there is provided a method of displaying stereoscopic information related to an ultrasound sectional plane of a target object, the method including: setting a line of interest on the target object; obtaining brightness information of the ultrasound sectional plane of the target object along the set line of interest; converting the obtained brightness information into height information; and displaying the stereoscopic information related to the ultrasound sectional plane of the target object based on the height information.

The stereoscopic information related to the ultrasound sectional plane of the target object may include depth information, capture time information, and brightness information of the ultrasound sectional plane of the target object.

The setting may include: receiving an input for setting the line of interest; and based on the received input, determine the line of interest based on at least one from among an ultrasound scan line and a line extending at a predetermined angle on an ultrasound image regarding the target object.

The converting may include: mapping the obtained brightness information including predetermined gray scale values to height values of a predetermined range.

The converting may include: allocating predetermined colors to the mapped height values.

The allocating may include: setting a color distribution with respect to the predetermined range of the mapped height values; and allocating colors for corresponding height values according to the set color distribution.

The displaying may include: displaying the information related to the ultrasound sectional plane in a stereoscopic space by using the depth information as a first axis, the capture time information as a second axis, and the height information converted from the brightness information as a third axis.

According to an aspect of another exemplary embodiment, there is provided an apparatus for displaying stereoscopic information related to an ultrasound sectional plane of a target object, the apparatus including: a line setting unit which sets a line of interest on the target object; a brightness information obtaining unit which obtains brightness information of the ultrasound sectional plane of the target object along the set line of interest; an information converting unit which converts the obtained brightness information into height information; and a display unit which displays the stereoscopic information related to the ultrasound sectional plane of the target object based on the height information.

The stereoscopic information related to the ultrasound sectional plane of the target object may include depth information, capture time information, and brightness information of the ultrasound sectional plane of the target object.

The apparatus may further include: an input receiving unit which receives an input for setting the line of interest, wherein the line setting unit, based on the received input, determines the line of interest based on at least one from among an ultrasound scan line and a line extending at a predetermined angle on an ultrasound image regarding the target object.

The information converting unit may include: a mapping unit which maps the obtained brightness information including predetermined gray scale values to height values of a predetermined range.

The information converting unit may include: a color allocating unit which allocates predetermined colors to the mapped height values.

The color allocating unit may include: a distribution setting unit which sets a color distribution with respect to the predetermined range of the height values, wherein the color allocating unit allocates colors for corresponding height values according to the set color distribution.

The display unit may display the information related to the ultrasound sectional plane in a stereoscopic space by using the depth information as a first axis, the capture time information as a second axis, and the height information converted from the brightness information as a third axis.

According to an aspect of another exemplary embodiment, there is provided a non-transitory computer readable recording medium having embodied thereon a program for executing the above-described method.

According to an aspect of still another exemplary embodiment, there is provided an ultrasound imaging apparatus including an input unit configured to receive a two-dimensional (2D) ultrasound image of a target object and a controller configured to convert the 2D ultrasound image to a three-dimensional (3D) ultrasound image by using a depth map having depth information corresponding to brightness information of the 2D ultrasound image.

According to an aspect of still another exemplary embodiment, there is provided an ultrasound imaging apparatus for converting a two-dimensional (2D) ultrasound image of a target object into a three-dimensional (3D) ultrasound image of the target object, the ultrasound imaging apparatus including at least one microprocessor to implement a brightness obtaining unit configured to obtain brightness information of an ultrasound sectional plane image of a target object along a predetermined scan line and an information conversion unit configured to convert the obtained brightness information into depth information, wherein the 3D ultrasound image of the target object is obtained based on the converted depth information.

BRIEF DESCRIPTION OF THE DRAWINGS

The above and other features will become more apparent by describing in detail exemplary embodiments thereof with reference to the attached drawings in which.

DETAILED DESCRIPTION

Hereinafter, exemplary embodiments will now be described more fully with reference to the accompanying drawings. The exemplary embodiments may, however, be embodied in many different forms and should not be construed as being limited to the embodiments set forth herein; rather, these embodiments are provided so that this disclosure will be thorough and complete, and will fully convey the scope of the disclosure to those skilled in the art. For example, configuring elements that are singular forms may be executed in a distributed fashion, and also, configuring elements that are distributed may be combined and then executed. In the following description, well-known functions or constructions are not described in detail since they would obscure the disclosure with unnecessary detail. Also, throughout the specification, like reference numerals in the drawings denote like elements.

Most terms used in this specification are general terms well known in the art and defined in consideration of functions, however, some terms may vary according to intention of those of ordinary skill in the art, usual practices, or introduction of new technologies in the art. Also, specified terms may be selected by the applicant at his or her discretion, and in this case, the detailed meanings thereof will be described in relevant parts of the description herein. Thus, the terms used in the specification should not be understood as simple names but based on the substantial meanings of the terms and the overall description herein.

Throughout the specification, it will also be understood that when a component "includes" or "comprises" an element, unless there is a particular description contrary thereto, it should be understood that the component does not exclude another element but may further include another element. In addition, terms such as "unit", "module", or the like are used refer to units that perform at least one function or operation, and the units may be implemented as hardware or software or as a combination of hardware and software.

Throughout the specification, an "ultrasound image" refers to an image of a target object obtained using an ultrasonic wave. The target object may refer to a portion of a body. For example, the target object may be an organ such as a liver, a heart, a uterus, a brain, a breast, or a stomach, or may be an embryo.

The ultrasound image may be obtained in various ways. For example, the ultrasound image may be at least one of a brightness (B) mode image, a color (C) mode image, a doppler (D) mode image, and a motion (M) mode image. Also, according to an exemplary embodiment, the ultrasound image may be a 2-dimensional (2D) image or a 3-dimensional (3D) image.

Throughout the specification, a "user" may refer to a medical specialist such as a doctor, a nursing staff, a clinical pathologist, or a medical imaging specialist, but not limited thereto.

Expressions such as "at least one of," when preceding a list of elements, modify the entire list of elements and do not modify the individual elements of the list.

Figure 1:
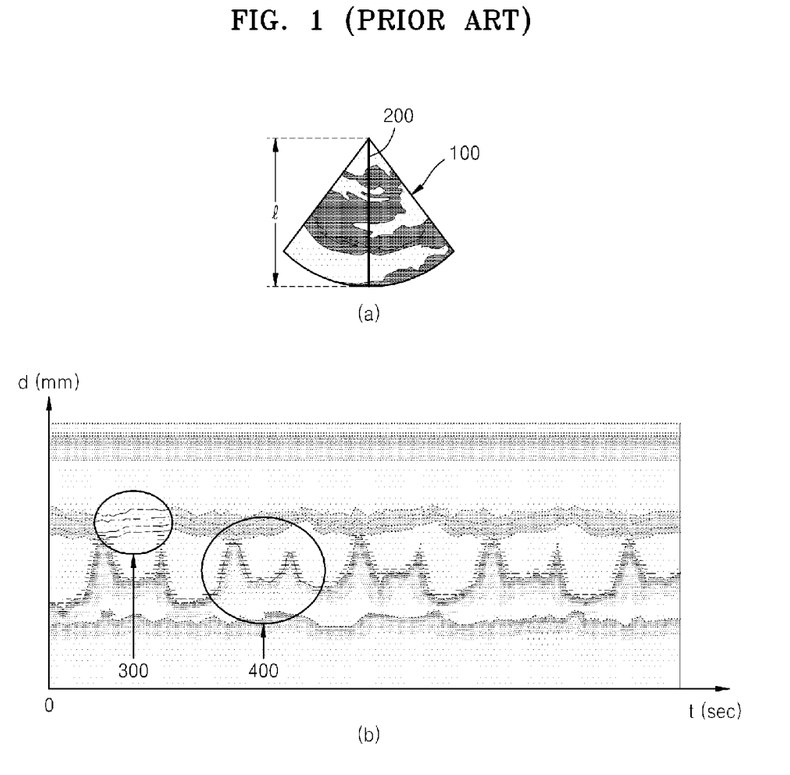
FIG. 1 illustrates two-dimensional (2D) information related to an ultrasound sectional plane of a target object according to the related art.

FIG. 1 illustrates 2D information related to an ultrasound sectional plane of a target object according to the related art. Information, as shown in (b), regarding tissue of the target object with respect to the ultrasound sectional plane obtained along a scan line 200 may be obtained from an ultrasound image 100, as shown in (a), of the target object. For example, in a case where an ultrasound apparatus operates in an M mode, location and motion information of tissue detected along the scan line 200 may be 2-dimensionally represented with respect to a capture time of the ultrasound image 100.

Referring to FIG. 1, a motion of tissues detected along the scan line 200 in the ultrasound image 100 of, for example, a heart, may be obtained based on location information d of tissues captured with respect to a time t and represented as a brightness value. In FIG. 1, the scan line 200 has a length l, and thus, a maximum value of the location information d of tissues along the scan line 200 in the ultrasound image 100 may correspond to the length I of the scan line 200.

In other words, an M mode image may be 2-dimensionally displayed as a brightness value relative to the time t (e.g., a time axis) and location information d (e.g., a depth axis). For example, as shown in FIG. 1, the information regarding the ultrasound sectional plane of the target object may be displayed as different brightness values according to the capture time t and a location of corresponding tissue.

Thus, a related art method provides the information regarding the ultrasound sectional plane of the ultrasound image 100 as the brightness value. Therefore, data analysis and measurement results regarding the ultrasound image 100 may be varied according to a resolution of the ultrasound image and a skill level of a user of the ultrasound apparatus. For example, in a case where a brightness value of tissue is not known, as shown in 300 of FIG. 1, or a degree of definition of tissue is lower, as shown in 400 of FIG. 1, accuracy and utility of the ultrasound image 100 may be significantly reduced and reliability of data analysis and measurement of the ultrasound image 100 are also reduced.

Further, since a range of a brightness value which can be recognized by a human eye is limited, the data analysis and measurement result may not be accurate. To compensate for such limitation, for example, a higher resolution, a higher definition image, or a more accurate display method may be required.

Therefore, exemplary embodiments may provide a method of displaying stereoscopic information related to the ultrasound sectional plane of the ultrasound image 100 using a brightness value, such that analysis and measurement of data may be performed more accurately compared to the related art.

Furthermore, exemplary embodiments may facilitate analysis of data by using a color in representing brightness information of an ultrasound sectional plane of the target object. Also, exemplary embodiments may adjust a color distribution when detailed observation is desired, thereby enhancing representation and accurate analysis of data.

Figure 2:
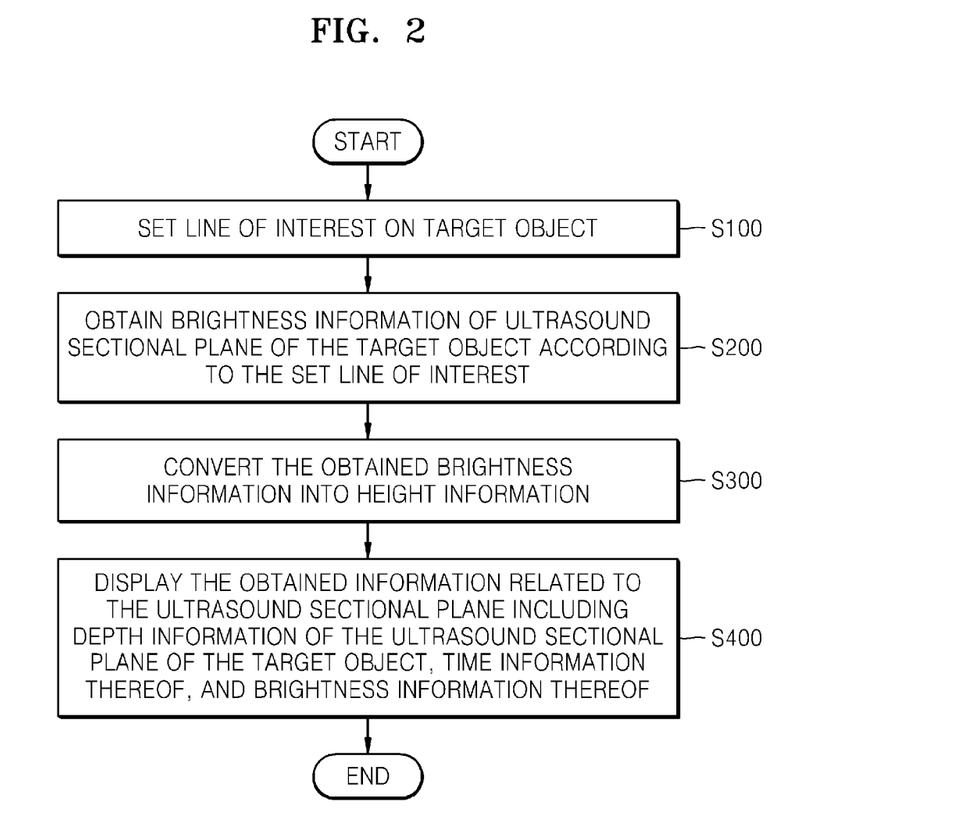
FIG. 2 is a flowchart illustrating a method of displaying stereoscopic information related to an ultrasound sectional plane of a target object according to an exemplary embodiment.

FIG. 2 is a flowchart illustrating a method of displaying stereoscopic information related to an ultrasound sectional plane of a target object according to an exemplary embodiment.

Figure 3:
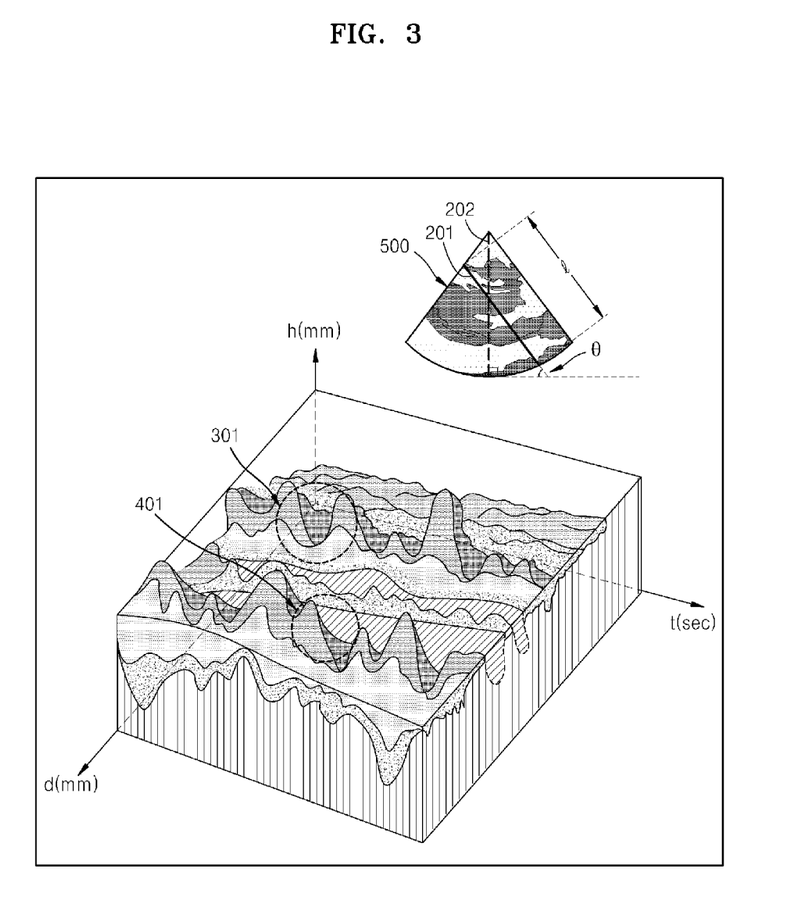
FIG. 3 illustrates stereoscopic information related to an ultrasound sectional plane of a target object according to an exemplary embodiment.

FIG. 3 illustrates stereoscopic information related to an ultrasound sectional plane of a target object according to an exemplary embodiment.

Referring to FIG. 2, the method of displaying stereoscopic information related to an ultrasound sectional plane of a target object according to an exemplary embodiment may include setting a line of interest on a target object (operation S100), obtaining brightness information of the ultrasound sectional plane of the target object according to the set line of interest (operation S200), converting the obtained brightness information into height information (operation S300), and displaying the stereoscopic information related to the ultrasound sectional plane of the target object based on the converted height information (operation S400).

The information related to the ultrasound sectional plane may include, but not limited thereto, depth information, capture time information, and brightness information of the ultrasound sectional plane of the target object. Here, as shown in FIG. 3, the information related to the ultrasound sectional plane may be represented in a 3-dimensional manner using a depth axis, a height axis, and a time axis.

An ultrasound image 500 of the target object may include a substantially arc-shaped image such as, for example, an image obtained by using a convex probe, a substantially rectangular image such as, for example, an image obtained by using a linear probe, etc. For illustrative purposes, it is illustrated in FIG. 3 that the ultrasound image 500 has a substantially arc-shaped image.

Figure 4:
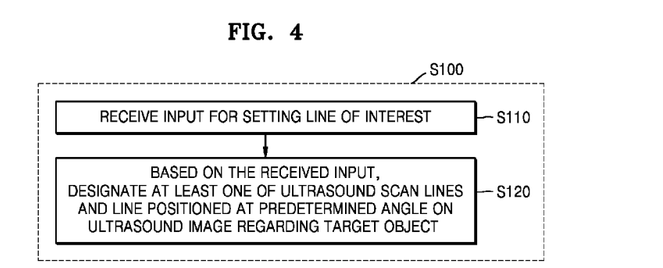
FIG. 4 illustrates a method of setting a line of interest according to an exemplary embodiment.

FIG. 4 illustrates a method of setting a line of interest according to an exemplary embodiment.

Referring to FIG. 4, setting the line of interest on the target object (operation S100) of FIG. 2 may include receiving an input for setting the line of interest (operation S110) and, based on the received input, designating at least one of an ultrasound scan line and a line extending at a predetermined angle on an ultrasound image of the target object as the line of interest (operation S120).

Referring to FIG. 3, the line of interest may include at least one of an ultrasound scan line and a line 201 extending at a predetermined angle θ on the ultrasound image 500 according to the input.

The input may be received from outside of an ultrasound apparatus by using a signal input unit such as a keyboard, a mouse, a joystick, etc., and may be previously stored in a storage (not shown) connected to an input receiving unit of the ultrasound apparatus or applied in real time to the ultrasound apparatus during a process of obtaining the ultrasound image 500. In an exemplary embodiment, the storage may be a memory.

The line 201 extending at the predetermined angle θ on the ultrasound image 500 may be used to obtain an ultrasound sectional plane of the target object at the predetermined angle θ. For example, the predetermined angle θ may be an angle formed by the line 201 and a tangential line at a lowest end portion of the ultrasound image 500. For example, as shown in FIG. 3, in a case where the designated line is a center scan line 202 among ultrasound scan lines, the predetermined angle θ may be a right angle perpendicular to a tangential line at the lowest portion of the ultrasound image 500.

Also, the predetermined angle θ may be determined as 180 degree when the designated line and the lower end portion of the ultrasound image 500 are parallel to each other. In this case, the center scan line 202 may be perpendicular to the line 201.

When the line of interest is set, the information related to the ultrasound sectional plane of the target object may be obtained according to the set line of interest. The information related to the ultrasound sectional plane may include depth information d, capture time information t, and brightness information of the ultrasound sectional plane of the target object. In an exemplary embodiment, the brightness information may be converted into height information to be displayed in stereoscopic information, as described above.

The depth information d of the ultrasound sectional plane may include location information of tissue of the target object included in the ultrasound sectional plane along the line of interest on the ultrasound image 500. For example, as shown in an axis d of FIG. 3, a location of the tissue of the target object included in the ultrasound sectional plane may be relatively determined with respect to a start point of the designated line in the ultrasound image 500, and the location information of the tissue of the target object may be represented as the depth information d of the ultrasound sectional plane. For example, the depth information of the start point is zero and the depth information of an end point may correspond to a length I of the designated line. The depth information d of the ultrasound sectional plane may be represented in millimeters (mm), but not limited thereto.

The capture time information t of the ultrasound sectional plane may include information regarding a time at which the ultrasound image 500 is obtained. For example, the time information t of the ultrasound sectional plane may include an ultrasound capture time of the target object. The time information t of the ultrasound sectional plane may be represented in seconds (sec), but not limited thereto.

The information related to the ultrasound sectional plane may include the brightness information of the ultrasound sectional plane. For example, to observe movements of heart muscles and valves in an ultrasound image of the heart, a line of interest may be set on the ultrasound image of the heart and the depth information d of the ultrasound sectional plane of the target object, i.e., the heart, may be measured with respect to time along the set line of interest on the ultrasound sectional plane of the heart. Accordingly, the information related to the ultrasound sectional plane with respect to the heart may be obtained.

A change in the brightness of an ultrasound image at the same location, i.e., having the same depth, with respect to time represents movements of a target object, e.g., the heart muscles and valves. In other words, the change in the brightness of the ultrasound image with respect to time may represent the movement of heart muscles and valves with respect to time. As shown in 301 and 401 of FIG. 3, by using the brightness information indicating the movements of corresponding tissue of the target object, boundaries of tissues and degrees of movements thereof may be more clearly identified.

Figure 5:
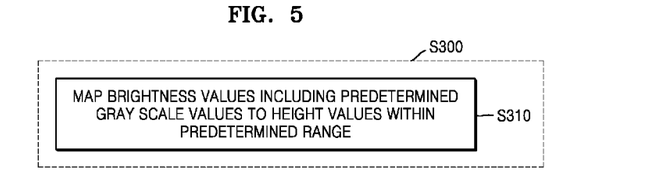
FIG. 5 illustrates a method of converting brightness information of an ultrasound sectional plane into height information thereof according to an exemplary embodiment.

FIG. 5 illustrates a method of converting the brightness information of an ultrasound sectional plane into the height information h according to an exemplary embodiment.

The operation of converting the obtained brightness information into the height information h (operation S300) of FIG. 2 may include mapping brightness values including predetermined gray scale values to height values within a predetermined range (operation S310).

For example, the brightness information of the ultrasound sectional plane may be defined as gray scale values from 0 to 255, but not limited thereto. Alternatively, the brightness information of the ultrasound sectional plane may be defined as gray scale values from 0 to 511, but not limited thereto.

The height information h may include information regarding height values to which the gray scale values are mapped and information regarding colors used to represent the corresponding height values. The height values of the height information h may be represented in millimeters (mm), but not limited thereto.

In the operation of mapping the brightness values including predetermined gray scale values to the height values within a predetermined range (operation S310) according to an exemplary embodiment, gray scale values, for example, from 0 to 255 may be mapped to the height information h having height values, for example, from 0 mm to 255 mm. However, it should be noted that this is merely an example and the height information h may have different height values corresponding to the gray scale values.

For example, in a case where a gray scale value "0" is defined as a gray scale value indicating a black color that is a darkest color value, the gray scale value "0" may be mapped to, for example, a lowest value of the height information h. In a case where a gray scale value "255" is defined as a gray scale value indicating a white color that is a brightest color value, the gray scale value "255" may be mapped to, for example, a highest value of the height information h.

On the other hand, in a case where the gray scale value "0" is used as a gray scale value indicating the white color that is the brightest color value, the brightest color value may be mapped to, for example, the lowest value of the height information h, and in a case where the gray scale value "255" is a gray scale value indicating the black color that is the darkest color value, the darkest color value may be mapped to, for example, the highest value of the height information h.

Alternatively, in the operation of mapping the gray scale values to the height values within the predetermined range (operation S310), gray scale values from 0 to 511 may be mapped to height information h having height values from 0 to 255. Here, for example, in a case where gray scale values exceeding 255 are rare, the gray scale values exceeding 255 may be collectively mapped to the height value of 255. Accordingly, mapping of the height information h may be efficient in that additional height values are not required to represent the rare gray scale values.

Figure 6:
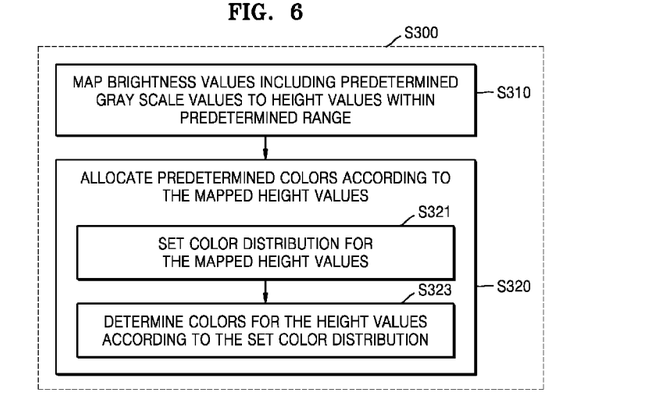
FIG. 6 illustrates a method of allocating colors corresponding to height information according to an exemplary embodiment.

FIG. 6 illustrates a method of allocating colors corresponding to the height information h according to an exemplary embodiment.

The operation of converting the obtained brightness information into the height information h (operation S300) according to an exemplary embodiment may include allocating predetermined colors according to mapped height values (operation S320).

For example, a plurality of different colors may be allocated according to the height values that are mapped in operation S310 (operation S320). In an exemplary embodiment, seven colors such as, for example, black, purple, blue, green, yellow, orange, and red, may be respectively allocated to predetermined ranges of height values. That is, for example, the black color may be allocated to a range of height values from 0 to 36 among the height values 0 to 255, the purple color may be allocated to a range of height values from 37 to 73, and the blue color may be allocated to a range of height values from 74 to 110, etc.

In an exemplary embodiment, three or more different colors may be uniformly allocated to the height values.

In a case where colors are allocated with respect to a range of height values, an allocation status of colors with respect to a range of height values may be provided as a bar on a screen. This will be described in detail later with reference to FIGS. 7A to 7C.

Also, as shown in FIG. 6, the operation of allocating predetermined colors according to the mapped height values (operation S320) according to an exemplary embodiment may include setting a color distribution among the height values (operation S321) and determining colors for corresponding height values according to the set color distribution (operation S323).

Figure 7A:
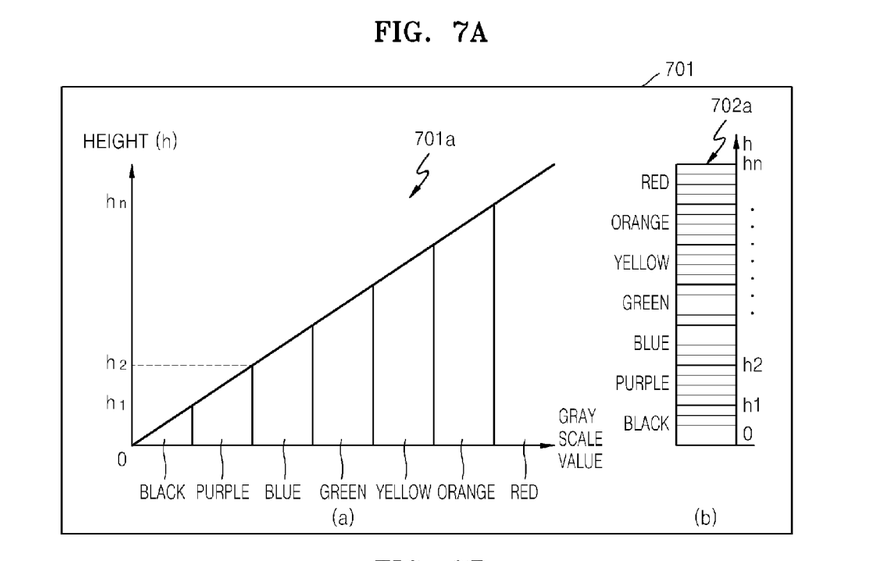
FIGS. 7A through 7C illustrate graphs for explaining mapping gray scale values to height values and status bars for explaining a color distribution with respect to height information according to an exemplary embodiment.
Figure 7B:
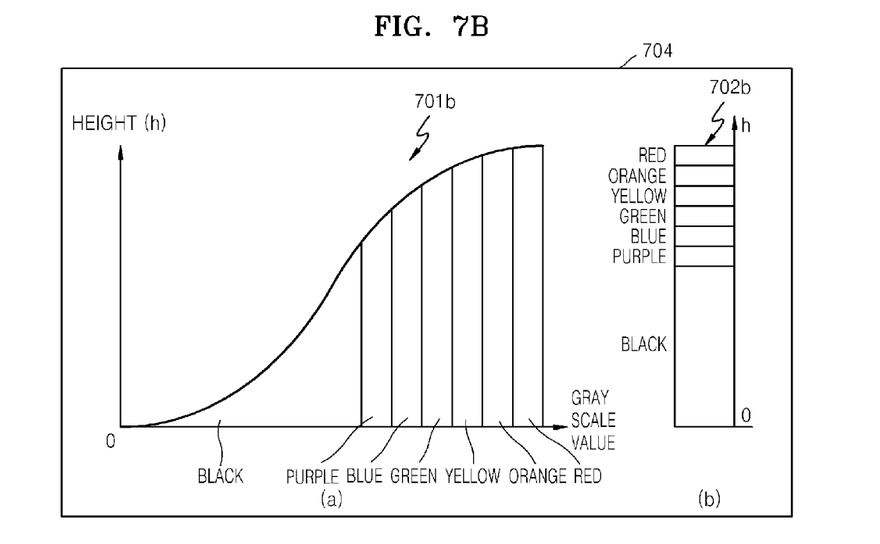
Figure 7C:
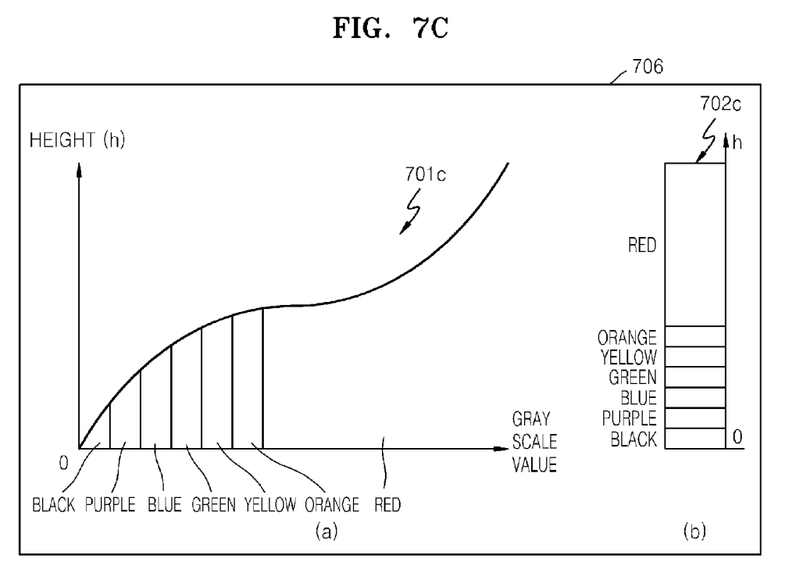

FIGS. 7A through 7C illustrate graphs for explaining mapping gray scale values to height values and status bars for explaining a color distribution with respect to height information according to an exemplary embodiment.

Referring to FIG. 7A, a graph, as shown in (a), shows a mapping relationship 701*a* between gray scale values and height values, in which gray scale values are substantially proportionally mapped to the height values. Colors substantially uniformly distributed with respect to height values according to a uniform color distribution method may also be provided in a form of a bar 702*a* on a screen. For example, the uniform color distribution may be previously set as default in a storage (not shown) of an ultrasound apparatus.

The gray scale mapping and color distribution may be differently determined according to different ranges of height values. Referring to FIG. 7B, for example, a graph 701*b*, as shown in (a), shows a mapping relationship between the gray scale values and the height values, in which gray scale values are disproportionally mapped to height values, i.e., the mapping has a greater slope of increase in lower gray scale values than higher gray scale values. Also, a status bar 702*b*, as shown in (b), may be provided, in which colors are distributed among height values such that more colors are allocated to higher height values than lower height values. That is, the higher height values may be represented in more variety of colors. Referring to FIG. 7C, a graph 701c, as shown in (a), shows a mapping relationship 701c between the gray scale values and the height values, in which gray scale vales are disproportionally mapped to height values, i.e., the mapping has a greater slope of increase in higher gray scale values than lower gray scale values. Also, a status bar 702c, as shown in (b), may be provided, in which colors are distributed among height values such that more colors are allocated to lower height values than higher height values. That is, the lower height values may be represented in more variety of colors.

Thus, in an exemplary embodiment, more colors may be distributed among higher brightness values of the ultrasound image of the target object, as shown in the graph 701b of FIG. 7B, and thus a brighter part in the ultrasound image may be more finely displayed in various colors. In other words, a plurality of colors are densely distributed in a part corresponding to higher brightness values, thereby facilitating observation and analysis of a corresponding part by using a more rapid color change with respect to a height change.

Also, in another exemplary embodiment, more colors may be distributed among lower brightness values of the ultrasound image of the target object, as shown in the graph 701c of FIG. 7C, and thus a darker part in the ultrasound image may be displayed in various colors (702c), thereby facilitating observation and analysis of a corresponding part by using a more rapid color change with respect to a height change.

Referring to FIG. 2, the operation of displaying the stereoscopic information related to the ultrasound sectional plane of the target object based on the height information h (operation S400) may include displaying the stereoscopic information related to the ultrasound sectional plane in a stereoscopic space by using the depth information d as a first axis, the capture time information t as a second axis, and the brightness information as a third axis. For example, as shown in FIG. 3, the stereoscopic information related to the ultrasound sectional plane may be displayed with respect to a plane formed by an axis of the depth information d, an axis of the capture time information t, and a height axis of brightness values of the ultrasound sectional plane of the target object.

Figure 8:
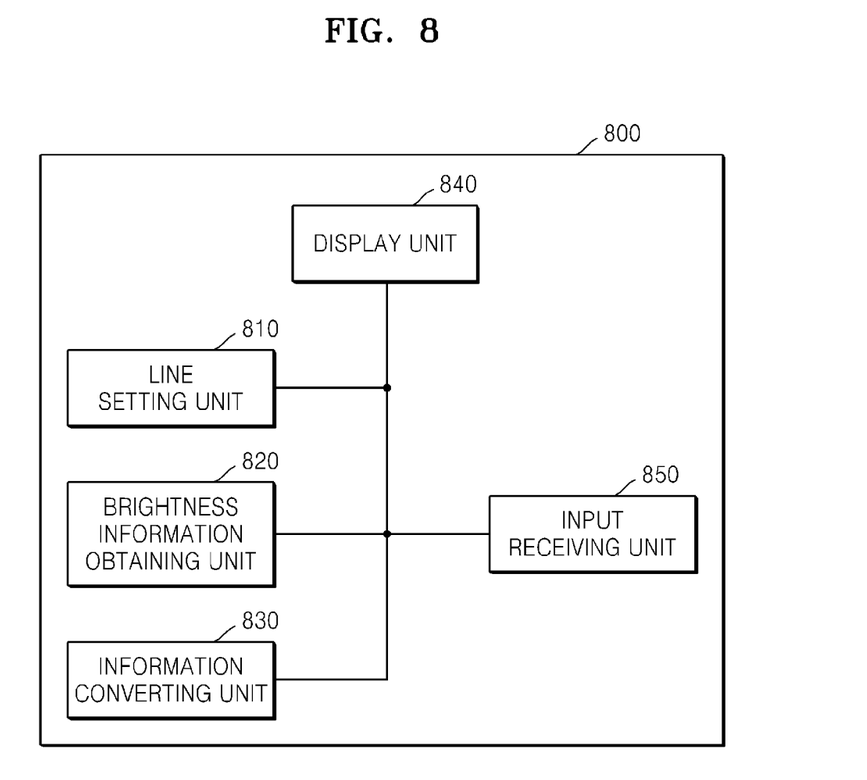
FIG. 8 is a block diagram of an apparatus for displaying stereoscopic information related to an ultrasound sectional plane of a target object according to an exemplary embodiment.

FIG. 8 is a block diagram of an apparatus 800 for displaying stereoscopic information related to an ultrasound sectional plane of a target object according to an exemplary embodiment.

Referring to FIG. 8, the apparatus 800 according to an exemplary embodiment may include a line setting unit 810, a brightness information obtaining unit 820, an information converting unit 830, and a display unit 840.

The apparatus 800 according to an exemplary embodiment may further include an input receiving unit 850 for receiving an input.

The information related to the ultrasound sectional plane may include depth information d, the capture time information t, and the brightness information of the ultrasound sectional plane of the target object.

The image obtaining unit (not shown) may obtain the ultrasound image 500 with respect to the target object by using, for example, an echo signal obtained by irradiating ultrasonic waves to the target object. The ultrasound image 500 of the target object may include a substantially arc-shaped image such as, for example, an image obtained by using a convex probe, a rectangular image such as, for example, an image obtained by using a linear probe, etc. The obtained ultrasound image 500 may be displayed on the display unit 840.

The line setting unit 810 may set a line of interest on the ultrasound image 500 of the target object. The line of interest may be set based on an input received through the input receiving unit 850.

The brightness information obtaining unit 820 may obtain the information related to the ultrasound sectional plane including the brightness information of the ultrasound sectional plane of the target object along the set line of interest.

The information converting unit 830 may convert gray scale values indicating the brightness information of the ultrasound sectional plane into the height information h.

For example, the brightness information of the ultrasound sectional plane may be defined as gray scale values from 0 to 255 or from 0 to 511, but not limited thereto.

The height information h may include information regarding height values to which the gray scale values are mapped and information regarding colors used to represent the height values.

The display unit 840 may display the information related to the ultrasound sectional plane according to the set height information h. As shown in FIG. 3, the display unit 840 may display the information related to the ultrasound sectional plane in a stereoscopic space by using the depth information d as a first axis, the capture time information t as a second axis, and the brightness information as a third axis.

Meanwhile, when the display unit 840 is configured as a touch screen including a touch pad, the display unit 840 may be used as an input unit as well as an output unit. The display unit 840 may include, for example, a liquid crystal display (LCD), a thin film transistor-liquid crystal display (TFT-LCD), an organic light-emitting diode (OLED), a flexible display, a 3D display, or an electrophoretic display.

The input receiving unit 850 may receive an input for setting a line of interest. The input receiving unit 850 may include, for example, a key pad, a dome switch, a touch pad, a jog wheel, a jog switch, or the like, but not limited thereto. When the input receiving unit 850 is configured as a touch pad, the touch pad may be of, for example, a contact type electrostatic capacitive method, a pressure resistive layer method, an infrared ray sensing method, a surface ultrasonic wave conduction method, an integration type tension measurement method, a piezo effect method, or the like. When the display unit 840 is configured as the touch screen including a touch pad as described above, the touch screen may also operate as the input receiving unit 850, and thus the input receiving unit 850 may not be separately provided. In an exemplary embodiment, the input receiving unit 850 may also include a microphone for receiving an audio signal.

For example, an input may be received through a click or a touch on a predetermined button or the like provided on the input receiving unit 850. For example, an input may be received through a click of a line selection function button (not shown). Also, when the input receiving unit 850 is configured as a touch pad, an input may be received through a gesture such as a "tap", "double tap", "drag and drop", etc. An input may also be received in an audio form such as, for example, a user's voice.

Here, the line setting unit 810, the brightness information obtaining unit 820, and information converting unit 830 may be provided in separate controllers or integrated into a same controller (not shown). The controller may be, for example, a central processing unit (CPU).

Figure 9:
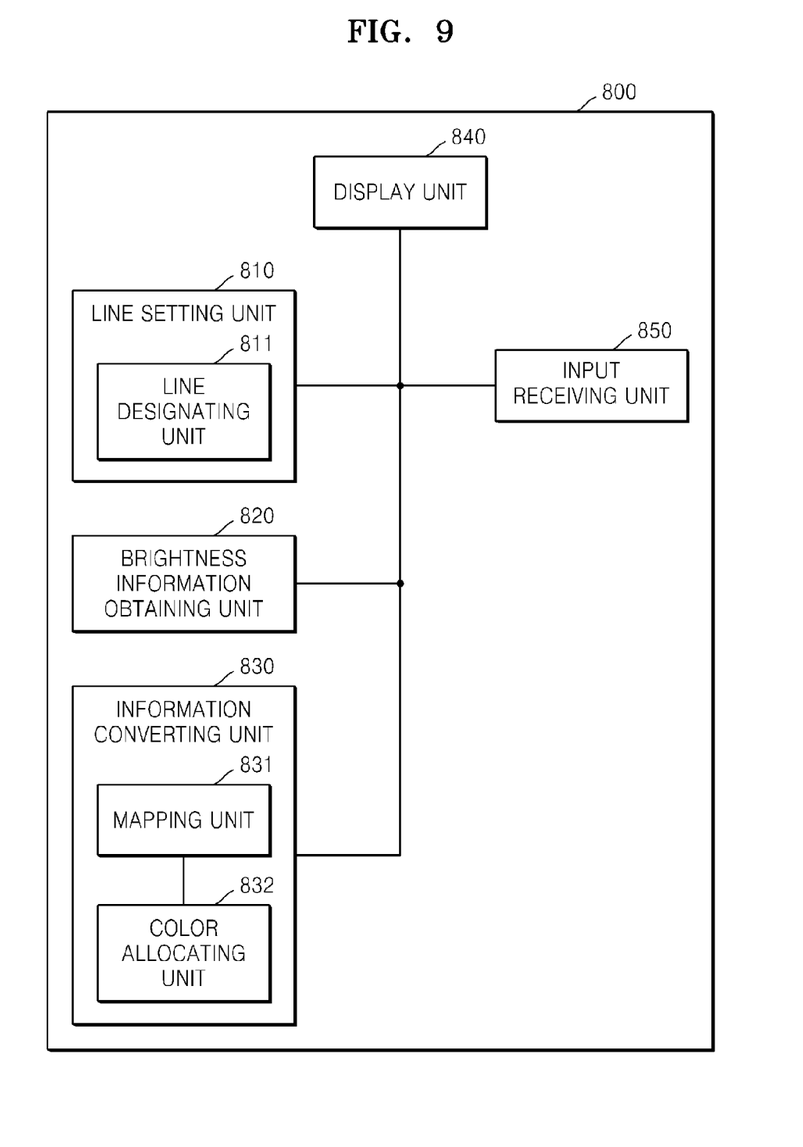
FIG. 9 is a detailed block diagram of an apparatus for displaying stereoscopic information related to an ultrasound sectional plane of a target object according to an exemplary embodiment.

FIG. 9 is a detailed block diagram of an apparatus for displaying stereoscopic information related to an ultrasound sectional plane of a target object according to an exemplary embodiment.

The line setting unit 810 may include a line designating unit 811 that designates a line of interest based on an input received from the input receiving unit 850.

The line of interest may include at least one of ultrasound scan lines and a line extending at a predetermined angle on the ultrasound image 500 according to the input from the input receiving unit 850.

The input may be received from outside of an ultrasound apparatus 800 through the input receiving unit 850. The input receiving unit 850 may be, for example, a keyboard, a mouse, a joystick, etc. The input may be previously stored in a storage (not shown) connected to the input receiving unit 850 of the ultrasound apparatus 800 or applied to the ultrasound apparatus 800 in real time during a process of obtaining the ultrasound image 500.

The brightness information obtaining unit 820 may obtain information related to an ultrasound sectional plane including brightness information of the ultrasound sectional plane of a target object along the designated set line of interest.

The information converting unit 830 may include a mapping unit 831 that maps gray scale values to height values according to a predetermined range thereof. The information converting unit 830 may further include a color allocating unit 832 that allocates colors to the mapped height values.

For example, the mapping unit 831 may map gray scale values from 0 to 255 to the height values from 0 to 255.

For example, in a case where a gray scale value "0" is defined as the gray scale value indicating a black color that is the darkest color value, the mapping unit 831 may map the gray scale value "0" to a lowest value of the height information h. In a case where a gray scale value "255" is defined as the gray scale value indicating a white color that is the brightest color value, the mapping unit 861 may map the gray scale value "255" to a highest value of the height information h.

On the other hand, in a case where the gray scale value "0" is used as the gray scale value indicating the white color that is the brightest color value, the mapping unit 831 may map the gray scale value "0", i.e., a brightest color value to the lowest value of the height information h, and the gray scale value "255" indicating the black color to the highest value of the height information h.

Also, for example, the mapping unit 831 may map gray scale values from 0 to 511 to the height values from 0 to 255. Here, for example, in a case where gray scale values exceeding 255 are rare, the gray scale values exceeding 255 may be collectively mapped to the height value of 255. Accordingly, mapping of the height information h may be efficient in that additional height values are not required to represent the rare gray scale values.

The color allocating unit 832 may allocate a plurality of different colors according to height values. In a case where colors are allocated to heights, the color allocating unit 832 may provide a color allocation status bar showing color allocation with respect to heights.

Figure 10:
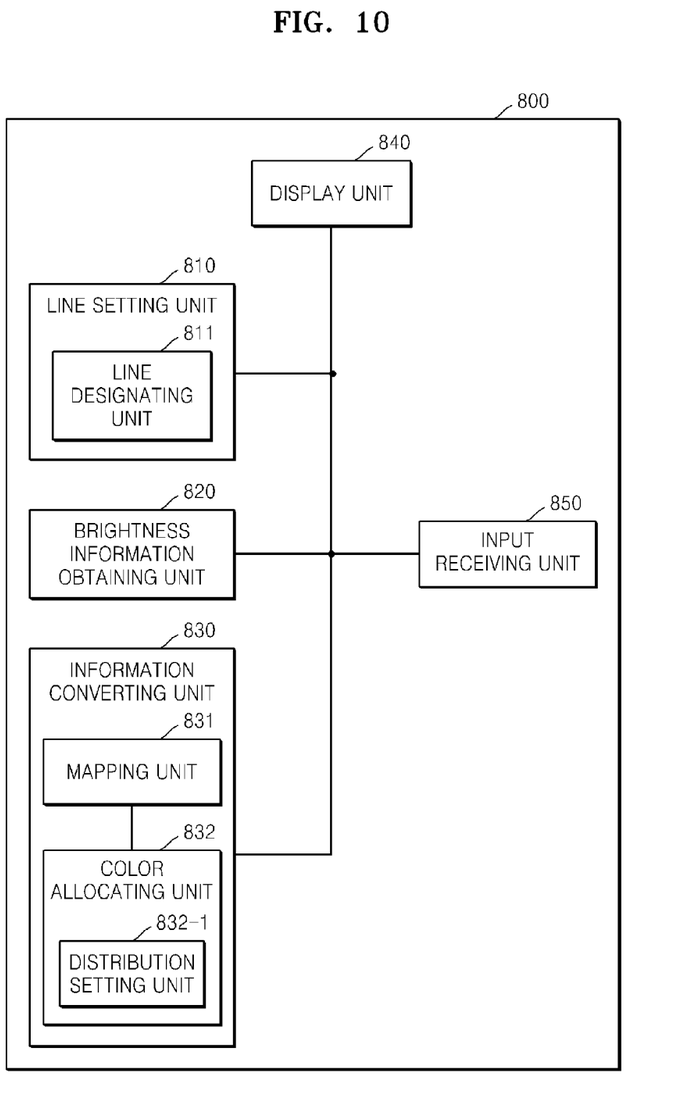
FIG. 10 is a further detailed block diagram of an apparatus for displaying stereoscopic information related to an ultrasound sectional plane of a target object according to an exemplary embodiment.

FIG. 10 is a further detailed block diagram of an apparatus for displaying stereoscopic information related to an ultrasound sectional plane of a target object according to an exemplary embodiment.

The color allocating unit 832 may further include a distribution setting unit 832-1 that sets a color distribution with respect to height values.

The distribution setting unit 832-1 may set different color distributions with respect to height values based on an input used to set a color distribution received from the input receiving unit 850.

In an exemplary embodiment, the color distribution may be differently set according to a user input.

Also, in an exemplary embodiment, the color distribution may be determined according to a previously set color distribution. For example, the previously set color distribution may represent an increased number of colors at height values to which higher brightness values are mapped. That is, if an ultrasound image of a target object includes a brighter part, the brighter part may be represented in a variety of colors, compared to a darker part.

The color allocating unit 832 may determine colors according to height values according to the set color distribution. In other words, as shown in FIGS. 7A through 7C, the color allocating unit 832 according to an exemplary embodiment may determine a color corresponding to each range of height values according to the set color distribution.

The description related to the above-described method may be applied to an apparatus according to an exemplary embodiment. Thus, the description of the apparatus as described with reference to the above-described method will not be repeated here.

The exemplary embodiments may be written as computer programs that may be implemented in general-use digital computers that execute the programs using a computer readable recording medium.

Examples of the computer readable recording medium include a read-only memory (ROM), a random-access memory (RAM), a compact disc read-only memory (CD-ROM), a magnetic tape, a floppy disk, an optical data storage device, etc. The computer readable recording medium may also be distributed over network coupled computer systems so that the computer readable code is stored and executed in a distributed fashion.

While a few embodiments have been particularly shown and described, it will be understood by those of ordinary skill in the art that various changes in form and details may be made therein without departing from the spirit and scope of the disclosure as defined by the appended claims and their equivalents. The exemplary embodiments should be considered in a descriptive sense only and not for purposes of limitation. Therefore, the scope of the invention is defined not by the detailed description of the invention but by the appended claims, and all differences within the scope will be construed as being included in the disclosure.

What is claimed is:

1. A method of displaying stereoscopic information related to an ultrasound sectional plane of a target object, the method comprising:
    setting a line of interest on the ultrasound sectional plane of the target object based on a received input;
    obtaining brightness information of the ultrasound sectional plane of the target object along the set line of interest;
    converting the obtained brightness information into height information; and
    displaying the stereoscopic information related to the ultrasound sectional plane of the target object based on the height information,
    wherein the stereoscopic information related to the ultrasound sectional plane of the target object comprises depth information, capture time information, and brightness information of the ultrasound sectional plane of the target object, and
    wherein the depth information includes information about a position of the target object along the set line of interest on the ultrasound sectional plane.

2. The method of claim 1, wherein the setting comprises:
    based on the received input, determining the line of interest based on at least one from among an ultrasound scan line and a line extending at a predetermined angle, the ultrasound scan line and the line being on the same ultrasound sectional plane.

3. The method of claim 1, wherein the converting comprises: mapping the obtained brightness information including predetermined gray scale values to height values of a predetermined range.

4. The method of claim 3, wherein the converting comprises: allocating predetermined colors to the mapped height values.

5. The method of claim 4, wherein the allocating comprises:
   setting a color distribution of the predetermined colors with respect to the predetermined range of the mapped height values; and
   allocating the predetermined colors to the displayed stereoscopic information according to the set color distribution.

6. The method of claim 1, wherein the displaying comprises: displaying the information related to the ultrasound sectional plane in a stereoscopic space by using the depth information as a first axis, the capture time information as a second axis, and the height information converted from the brightness information as a third axis.

7. An apparatus for displaying stereoscopic information related to an ultrasound sectional plane of a target object, the apparatus comprising:
   a line setting unit configured to set a line of interest on the ultrasound sectional plane of the target object based on a received input;
   a brightness information obtaining unit configured to obtain brightness information of the ultrasound sectional plane of the target object along the set line of interest;
   an information converting unit configured to convert the obtained brightness information into height information; and
   a display unit configured to display the stereoscopic information related to the ultrasound sectional plane of the target object based on the height information,
   wherein the stereoscopic information related to the ultrasound sectional plane of the target object comprises depth information, capture time information, and brightness information of the ultrasound sectional plane of the target object, and
   wherein the depth information includes information about a position of the target object along the set line of interest on the ultrasound sectional plane.

8. The apparatus of claim 7, further comprising: an input receiving unit configured to receive the input for setting the line of interest,
   wherein the line setting unit, based on the received input, determines the line of interest based on at least one from among an ultrasound scan line and a line extending at a predetermined angle, the ultrasound scan line and the line being on the same ultrasound sectional plane.

9. The apparatus of claim 7, wherein the information converting unit comprises: a mapping unit configured to map the obtained brightness information including predetermined gray scale values to height values of a predetermined range.

10. The apparatus of claim 9, wherein the information converting unit comprises: a color allocating unit configured to allocate predetermined colors to the mapped height values.

11. The apparatus of claim 10, wherein the color allocating unit comprises: a distribution setting unit configured to set a color distribution of the predetermined colors with respect to the predetermined range of the mapped height values,
   wherein the color allocating unit allocates the predetermined colors to the displayed stereoscopic information according to the set color distribution.

12. The apparatus of claim 7, wherein the display unit displays the information related to the ultrasound sectional plane in a stereoscopic space by using the depth information as a first axis, the capture time information as a second axis, and the height information converted from the brightness information as a third axis.

13. A non-transitory computer readable recording medium having recorded thereon on a program for executing the method of claim 1.

14. The method of claim 5, wherein the color distribution is substantially uniform among the predetermined range of the mapped height values.

15. The method of claim 5, wherein the color distribution is uneven among the predetermined range of the mapped height values.

16. The apparatus of claim 11, wherein the distribution setting unit sets the color distribution substantially uniform among the predetermined range of the mapped height values.

17. The apparatus of claim 11, wherein the distribution setting unit sets the color distribution unevenly among the predetermined range of the mapped height values.

* * * * *